(12) United States Patent
Yildirim et al.

(10) Patent No.: US 11,457,932 B2
(45) Date of Patent: Oct. 4, 2022

(54) ROBOTICALLY CONTROLLED WATER JET CUTTING

(71) Applicant: Mako Surgical Corp., Fort Lauderdale, FL (US)

(72) Inventors: Gokce Yildirim, Weehawken, NJ (US); Justin Joseph Gerges, Waldwick, NJ (US)

(73) Assignee: Mako Surgical Corp., Fort Lauderdale, FL (US)

( * ) Notice: Subject to any disclaimer, the term of this patent is extended or adjusted under 35 U.S.C. 154(b) by 533 days.

(21) Appl. No.: 16/273,582

(22) Filed: Feb. 12, 2019

(65) Prior Publication Data

US 2019/0282245 A1 Sep. 19, 2019

Related U.S. Application Data

(60) Provisional application No. 62/643,393, filed on Mar. 15, 2018.

(51) Int. Cl.
*A61B 17/16* (2006.01)
*A61B 34/10* (2016.01)
(Continued)

(52) U.S. Cl.
CPC .......... *A61B 17/1644* (2013.01); *A61B 34/10* (2016.02); *A61B 17/3203* (2013.01); *A61B 2017/1648* (2013.01); *A61B 2034/108* (2016.02); *B05B 1/3452* (2013.01); *B05B 7/12* (2013.01); *B05B 12/12* (2013.01); *B05B 12/124* (2013.01); *B24C 5/02* (2013.01);
(Continued)

(58) Field of Classification Search
CPC ............ A61B 17/3203; A61B 17/1644; A61B 2017/1648; A61B 34/30; A61B 34/10; A61B 2034/105; A61B 2034/108; B05B 12/12; B05B 12/124; B05B 12/082; B05B 12/084; B05B 9/0423; B05B 7/12; B05B 7/1218; B05B 1/3452; B05B 1/303006; B05B 1/323; B05B 11/007; B24C 5/02; G01B 11/27; B26D 5/00; B26F 2003/006; B26F 3/004
USPC ............ 606/79; 623/901, 908; 700/117, 195
See application file for complete search history.

(56) References Cited

U.S. PATENT DOCUMENTS 5,162,016 A 11/1992 Malloy
5,365,816 A 11/1994 Rudy
(Continued)

OTHER PUBLICATIONS

Honl, et al., "The Water Jet as a New Tool for Endoprosthesis Revision Surgery—An In Vitro Study on Human Bone and Bone Cement", Bio-Medical Materials and Engineering, vol. 13, No. 4, Jan. 2003, pp. 317-325.

*Primary Examiner* — Marcela I. Shirsat
(74) *Attorney, Agent, or Firm* — Lerner, David, Littenberg, Krumholz & Mentlik, LLP

(57) ABSTRACT

A cutting system includes a material removal tool having a fluid nozzle with an adjustable diameter, a workpiece including a target shape for removal, and a controller operable to adjust the diameter of the nozzle to vary fluid flow and control an amount of material removed by the material removal tool. The controller is adapted to adjust the nozzle to vary the fluid flow based on a position of the nozzle and workpiece data preoperatively obtained from the workpiece via a continuous feedback loop. A method of cutting a bone is also provided.

19 Claims, 8 Drawing Sheets

(51) Int. Cl.
 *B26F 3/00* (2006.01)
 *B24C 5/02* (2006.01)
 *A61B 17/3203* (2006.01)
 *B05B 7/12* (2006.01)
 *B05B 12/12* (2006.01)
 *B26D 5/00* (2006.01)
 *B05B 1/34* (2006.01)

(52) U.S. Cl.
 CPC ............... *B26D 5/00* (2013.01); *B26F 3/004* (2013.01); *B26F 2003/006* (2013.01)

(56) References Cited

U.S. PATENT DOCUMENTS

| | | | |
|---|---|---|---|
| 5,527,330 A | 6/1996 | Tovey | |
| 5,735,815 A | 4/1998 | Bair | |
| 5,868,056 A | 2/1999 | Pfarr et al. | |
| 5,871,462 A | 2/1999 | Yoder et al. | |
| 5,944,686 A | 8/1999 | Patterson et al. | |
| 6,216,573 B1 | 4/2001 | Moutafis et al. | |
| 6,375,635 B1 | 4/2002 | Moutafis et al. | |
| 6,701,174 B1 | 3/2004 | Krause et al. | |
| 6,711,432 B1 | 3/2004 | Krause et al. | |
| 6,757,582 B2 | 6/2004 | Brisson et al. | |
| 6,960,182 B2 | 11/2005 | Moutafis et al. | |
| 6,962,592 B2 | 11/2005 | Gatturna et al. | |
| 6,985,612 B2 | 1/2006 | Hahn | |
| 7,146,242 B2 | 12/2006 | Weinhofer | |
| 7,346,417 B2 | 3/2008 | Luth et al. | |
| 7,542,791 B2 | 6/2009 | Mire et al. | |
| 7,623,625 B2 | 11/2009 | Boyden et al. | |
| 7,627,085 B2 | 12/2009 | Boyden et al. | |
| 7,660,623 B2 | 2/2010 | Hunter et al. | |
| 7,711,089 B2 | 5/2010 | Boyden et al. | |
| 7,715,935 B2 | 5/2010 | Vogeley, Jr. et al. | |
| 7,724,871 B2 | 5/2010 | Boyden et al. | |
| 7,734,012 B2 | 6/2010 | Boyden et al. | |
| 7,742,567 B2 | 6/2010 | Boyden et al. | |
| 7,974,677 B2 | 7/2011 | Mire et al. | |
| 8,041,006 B2 | 10/2011 | Boyden et al. | |
| 8,057,396 B2 | 11/2011 | Forster et al. | |
| 8,142,987 B2 | 3/2012 | Ali et al. | |
| 8,147,859 B2 | 4/2012 | Palmaz et al. | |
| 8,268,340 B2 | 9/2012 | Choubey et al. | |
| 8,409,790 B2 | 4/2013 | Ali et al. | |
| 8,530,117 B2 | 9/2013 | Ali et al. | |
| 8,585,594 B2 | 11/2013 | Forster et al. | |
| 8,679,517 B2 | 3/2014 | Palmaz | |
| 8,750,960 B2 | 6/2014 | Boyce et al. | |
| 8,837,677 B2 | 9/2014 | Boyden et al. | |
| 8,932,347 B2 | 1/2015 | Choubey et al. | |
| 9,005,139 B2 | 4/2015 | Klaiman et al. | |
| 9,510,853 B2 | 12/2016 | Aljuri et al. | |
| 2003/0033044 A1* | 2/2003 | Bilyeu | G05B 13/024 700/117 |
| 2003/0068074 A1 | 4/2003 | Hahn | |
| 2004/0049198 A1 | 3/2004 | Gattuma et al. | |
| 2004/0068187 A1 | 4/2004 | Krause et al. | |
| 2004/0143269 A1 | 7/2004 | Pude et al. | |
| 2004/0157188 A1 | 8/2004 | Luth et al. | |
| 2004/0171924 A1 | 9/2004 | Mire et al. | |
| 2005/0100578 A1 | 5/2005 | Schmid et al. | |
| 2005/0227182 A1 | 10/2005 | Ali et al. | |
| 2006/0100498 A1* | 5/2006 | Boyce | A61B 6/505 600/408 |
| 2006/0162515 A1 | 7/2006 | Vogeley et al. | |
| 2006/0229550 A1 | 10/2006 | Staid et al. | |
| 2008/0009746 A1 | 1/2008 | Forster et al. | |
| 2008/0253520 A1 | 10/2008 | Boyden et al. | |
| 2008/0253522 A1 | 10/2008 | Boyden et al. | |
| 2008/0253525 A1 | 10/2008 | Boyden et al. | |
| 2008/0253526 A1 | 10/2008 | Boyden et al. | |
| 2008/0253527 A1 | 10/2008 | Boyden et al. | |
| 2008/0253528 A1 | 10/2008 | Boyden et al. | |
| 2008/0253529 A1 | 10/2008 | Boyden et al. | |
| 2008/0253530 A1 | 10/2008 | Boyden et al. | |
| 2008/0253531 A1 | 10/2008 | Boyden et al. | |
| 2008/0253627 A1 | 10/2008 | Boyden et al. | |
| 2009/0304772 A1 | 12/2009 | Choubey et al. | |
| 2011/0245859 A1 | 10/2011 | Klaiman et al. | |
| 2011/0251492 A1 | 10/2011 | Forster et al. | |
| 2011/0257653 A1 | 10/2011 | Hughes et al. | |
| 2011/0276127 A1 | 11/2011 | Forster et al. | |
| 2011/0282476 A1 | 11/2011 | Hegemier et al. | |
| 2012/0157829 A1 | 6/2012 | Boyden et al. | |
| 2012/0157830 A1 | 6/2012 | Boyden et al. | |
| 2013/0296812 A1* | 11/2013 | Bangera | A61B 18/0218 604/290 |
| 2014/0195030 A1 | 7/2014 | Farwell | |
| 2014/0294910 A1 | 10/2014 | Palmaz | |
| 2014/0309649 A1* | 10/2014 | Alvarez | A61B 34/30 606/107 |
| 2015/0025539 A1 | 1/2015 | Alvarez et al. | |
| 2015/0080717 A1 | 3/2015 | Ferko | |
| 2015/0119987 A1 | 4/2015 | Davignon et al. | |
| 2017/0000572 A1* | 1/2017 | Moctezuma de la Barrera | B25J 11/0055 |

\* cited by examiner

ROBOTICALLY CONTROLLED WATER JET CUTTING

CROSS-REFERENCE TO RELATED APPLICATIONS

This application claims the benefit of the filing date of U.S. Provisional Patent Application No. 62/643,393 filed Mar. 15, 2018, the disclosure of which is hereby incorporated herein by reference.

FIELD OF THE INVENTION

The present invention generally relates to water-jet cutting tools for bone resection, and more particularly to a system and method for controlling the water-jet cutting tools.

BACKGROUND OF THE INVENTION

In cementless orthopedic procedures, robust ingrowth is one key element to long term implant stability and performance. Biologic ingrowth requires sufficient stability of the implant with respect to adjacent bones and/or tissues particularly during the first 6-8 months after implantation. During this time, bone growth onto a roughened, or into a porous surface may only occur if the implant is held in a generally stable position, relative to the bone.

Since bone is heterogeneous and bone properties including bone density, porosity, and elastic modulus, for example, vary throughout the thickness of a particular bone, especially from the hard cortical bone to the spongy cancellous bone surrounded by the cortical bone, the success of fixation is generally dependent upon the specific implant and the properties of the bone that engage fixation features of the implant. As is disclosed in U.S. Pat. Pub. No. 2015/0119987, assigned to Applicant and incorporated herein by reference in its entirety, implant stability can be improved by designing the fixation features of the implant based on a preoperative determination of the particular bone properties that the fixation features will engage upon implantation. Although this implant specific design technique has proven successful in reducing micro-motion, stability of the implant is limited, in part, by the accuracy of the system preparing the bone resection.

Cemented and revision surgeries could also benefit from a more precise system. Particularly, a system capable of precisely controlling the depth of a cut to create particular cement curing pockets.

Prior to performing an implantation procedure, for example, a knee, hip, or shoulder replacement, a surgeon must resect a target bone using a working cutting tool, e.g., a saw, a drill, an energy beam such as a laser beam or an electron beam. Soft tissue surrounding the target site is often susceptible to damage when these traditional cutting tools are utilized, either from direct contact with the cutting tool, or excess heat emitted from the cutting tool. As a result, various retracting/protecting devices are required for shielding ligaments and soft tissue adjacent a cutting site. These devices, which require fixation to anatomical structures, complicate and/or lengthen the time of the procedure, and thus, increase the likelihood of human error. Moreover, excess heat can lead to bone necrosis, preventing proper bone ingrowth, which is vital to implant fixation, and particularly, cementless fixation. Furthermore, broaching, tamps, and form tools prepare cancellous bone by compacting the bone. When bone is compacted along a longitudinal axis, complications such as embolisms may arise.

Thus, there is a need for further improvements to the systems and methods of cutting bone, and in particular, for safely and efficiently resecting a bone and promoting bone ingrowth. Among other advantages, the present invention addresses these needs by providing a precise fluid jet cutting system configured to continuously control fluid pressure to minimize damage to the surrounding soft tissue and prevent the bone from overheating during cutting.

SUMMARY OF THE INVENTION

The fluid cutting system disclosed herein is particularly advantageous in cutting bone prior to a cementless implant procedure as the system minimizes, if not alleviates, several of the previously mentioned drawbacks associated with traditional saw and laser cutting. Specifically, fluid cutting systems are capable of creating a more precise and reproducible cut, especially when cutting a curved trajectory normal to a surface, than traditional saw or laser cutting systems. The fluid jet also keeps a cutting region of the bone cool during cutting, and therefore, greatly diminishes the risk of bone necrosis.

As is explained in detail hereinafter, the system is configured to control fluid cutting pressure via a continuous feedback loop such that a minimum pressure sufficient to cut through a particular section of bone can be utilized. By controlling fluid jet pressure in this manner, the depth of the cut can be precisely controlled to minimize damage of the soft tissue surrounding the cutting site such that fewer, if any, retracting/protecting devices are required. By adjusting the fluid nozzle, the system can direct the fluid radially outward, relative to a longitudinal axis of the bone, thus reducing the likelihood of an embolism arising from compacting bone along a longitudinal axis of the bone. The adjustability and versatility of the present system replaces the need for the use of numerous instruments, trials, and size specific cutting tools.

In one embodiment, the cutting system includes a material removal tool having a fluid nozzle with an adjustable diameter, a workpiece including a target shape for removal, and a controller operable to adjust the diameter of the nozzle to vary fluid flow and control an amount of material removed by the material removal tool. The controller is adapted to adjust the nozzle to control the fluid flow (i.e. cutting area, shape, and pressure) based on a position of the nozzle and workpiece data preoperatively obtained from the workpiece via a continuous feedback loop. The fluid utilized in the present invention may be water and/or a saline solution including antimicrobial agents, for example.

The cutting system may further include a sensor for continuously providing cut depth information. The controller is configured to adjust the nozzle to control the fluid flow based upon the cut depth information.

In a preferred embodiment, the material removal tool is coupled to a robotic arm via a drive mechanism provided on the material removal tool. Alternatively, the material removal tool may be manually operated.

The continuous feedback loop for controlling the fluid flow further includes at least one of a flow rate meter, a pump, a pressure gauge, and a throttle valve. The system further includes a fluid reservoir adapted for containing a fluid therein. The fluid reservoir is coupled to the material removal tool. The fluid reservoir may be filled with water or a saline solution.

A method of cutting a bone is also provided herein. The method includes obtaining bone quality data, operating a material removal tool including a nozzle having an adjustable diameter, and controlling the diameter of the nozzle to vary fluid flow based on a position of the nozzle and the obtained bone quality data via a continuous feedback loop. In a preferred embodiment, the material removal tool is coupled to a robotic arm via an instrument drive mechanism such that the nozzle of the material removal tool is spatially moveable relative to the bone. The bone may be a distal end of a femur bone.

The method may optionally include sensing cut depth information in real-time via a sensor such that the fluid control can be verified and modified if needed based on the cut depth information. The sensor may be an optical sensor or an ultrasonic sensor.

Tissue quality data, which may refer to bone quality data, being at least one of bone density, porosity, and elastic modulus, is obtained preoperatively. The bone quality data may be preoperatively derived from CT image data. In one particular embodiment, derivation of the bone quality data includes calculating one or more Houndsfield values from the CT image data with a density phantom to calculate real density values from any given scanning machine regardless of the radiology center scanning protocols.

BRIEF DESCRIPTION OF THE DRAWINGS

The present disclosure will be better understood on reading the following detailed description of embodiments thereof, and on examining the accompanying drawings, in which.

DETAILED DESCRIPTION

Although the disclosure set forth herein focuses on the use of cutting tools to cut and/or shape bone during surgery, it will be understood that the present invention may be used for a wide variety of applications where material is removed from a medium or stock workpiece.

By taking into account heterogeneous bone properties and preoperatively determining these properties, parameters of a bone resection can be designed to optimize a press-fit connection between a resected bone and an implant, such as an articular implant. An optimized press-fit between the resected bone and an articular implant may, for instance, reduce undesirable qualities, including excess micromotion, or maintain a desirable range for other qualities, including stress transmission and strain. The optimized press-fit is obtained by determining ideal engagement characteristics of fixation features of the articular implants, determining the parameters of a bone resection that would achieve the determined ideal engagement characteristics, and then safely and efficiently resecting the bone in view of these parameters.

Figure 1:
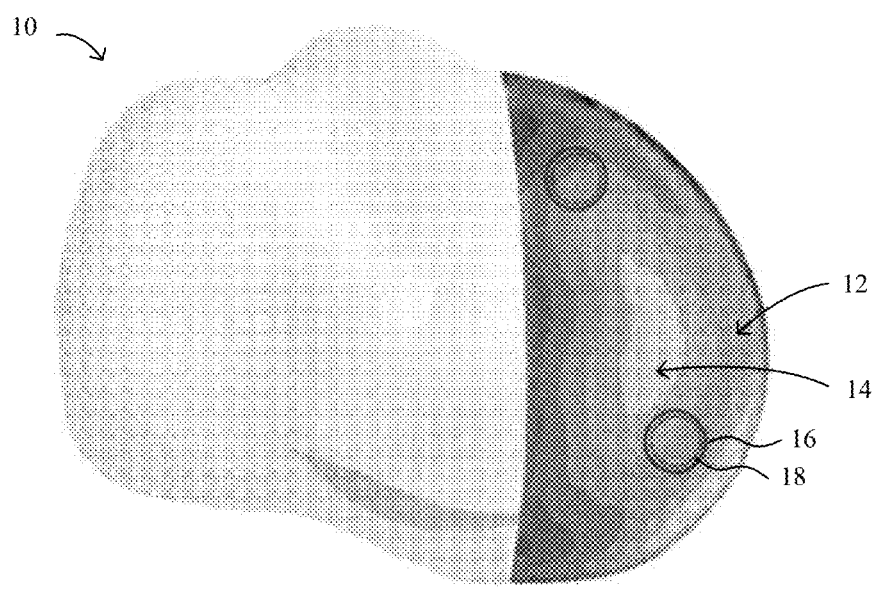
FIG. 1 is an example of an average bone density profile with a corresponding designed implant preparation.

FIG. 1 illustrates a bone having an exemplary average bone density profile 10. The bone density profile 10 exhibits areas of both relatively low density 12 (indicated by relatively dark shading) and relatively high density 14 (indicated by relatively light shading). FIG. 1 also illustrates an exemplary planned parameter of a bone resection 16 in order to achieve a press fit with a fixation feature having a corresponding shape. Outline 18 represents the size and shape of the fixation feature of the implant. Here, the planned parameter of the bone resection 16 is shown as having a circular cross-section. This particular resection may be made by plunging a rotating burr into the bone to a desired depth. In another embodiments (not shown), the resection 16 may be, for example, ovular in cross-section when viewed in the same plane, and formed if a rotating burr, for instance, is plunged into the bone at a preoperatively planned angle relative to the plane, or any other desirable cross-sectional shape. For instance, a planned parameter may include designing the resection based on preferred clearances and tolerances with particular fixation features that facilitate stability for cementless implants to improve long-term bone ingrowth/ongrowth to the implant.

Figure 2:
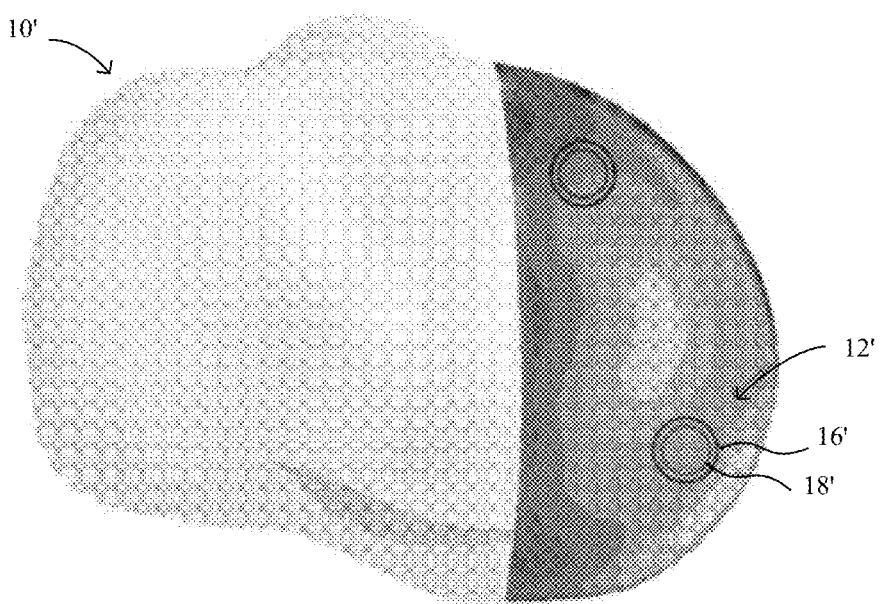
FIG. 2 is an example of a bone density profile exhibiting decreased density, and a corresponding implant preparation.

FIG. 2 illustrates a bone having an exemplary density profile 10' exhibiting decreased bone density compared to the bone density profile shown in FIG. 1. The bone density profile 10' exhibits increased areas of lower density 12' in planned fixation feature implant areas relative to bone 10 shown in FIG. 1. In order to achieve the designed press-fit between the fixation feature and the lower density bone 12', the planned parameter of the resection 16' is adjusted with respect to the shape of the fixation feature shown as outline 18'. Here, the parameter resection 16' has a smaller diameter compared to resection 16, thus increasing the interference between the fixation feature of the implant and the bone.

Figure 3:
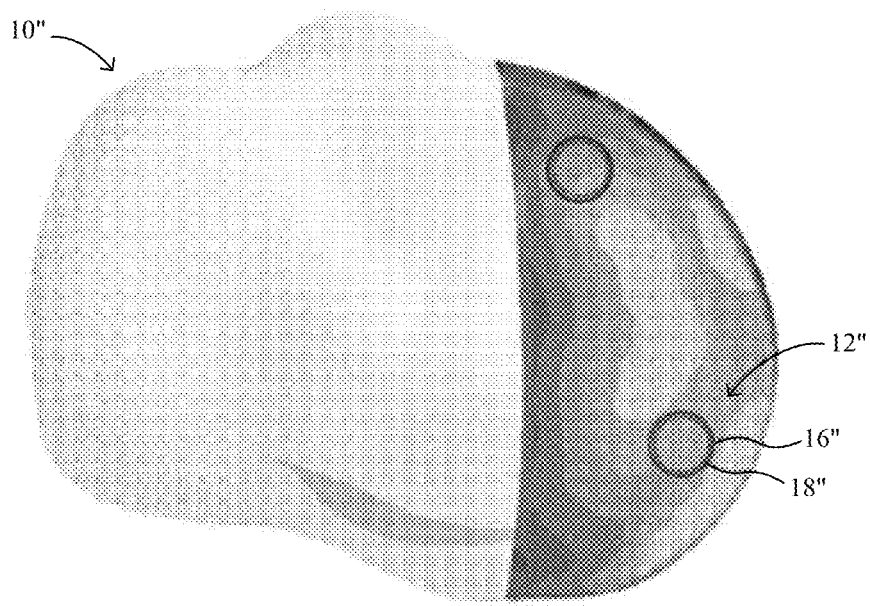
FIG. 3 is an example of a bone density profile exhibiting increased density, and a corresponding implant preparation.

FIG. 3 illustrates a bone having an exemplary density profile 10" exhibiting an increased bone density compared to the bone density profile shown in FIG. 1. The bone density profile 10" exhibits increased areas of higher density bone 14" in planned fixation feature implant areas relative to the bone shown in FIG. 1. In order to achieve the designed press-fit between the fixation feature and the bone, the parameters of the resection 16" are adjusted with respect to the shape of the fixation feature shown as outline 18". Here, the planned parameter of the resection 16" is modified to a larger diameter, thus decreasing the interference between the fixation feature and the bone.

Bone quality data, including bone density, of the heterogeneous bone may be derived from an image (or data relating to an image) of at least one joint. The image (or image data) can be obtained in a variety of manners, including by performing any medical imaging method known in the art, or by obtaining the image data from a collection and/or database. For example, the image data may be obtained by performing a CT scan. Additional suitable imaging methods include MRI, Electrical Impedance Tomography ("EIT"), Dual-Energy X-ray Absorptiometry ("DXA" or "DEXA"), X-ray, ultrasound, and nuclear imaging, for example. The image data may further comprise a combination of one or more different kinds of image data, for instance a composite image data that comprises both CT and MRI image data.

The image data obtained may correspond to either a single individual or to a population of individuals. For instance, the image data may correspond to a joint of the individual for whom the press-fit is being optimized. In this case, the parameters of the bone resection are determined on a patient-specific basis such that the parameters optimize the press-fit between the individual anatomy and the articular implant.

Bone quality may alternatively be derived from data representative of a population, for instance, a representative or average data corresponding to a particular population of individuals. The population may represent a class or sub-class of individuals, such as members of an age-range, a gender, a class of individuals who suffer from a particular joint or knee ailment, or any other relevant population. For example, the Stryker Orthopaedics Modeling and Analytics system ("SOMA") is a population-based design environment featuring a large database of bone morphology, including size, shape, density, and inner and outer cortical boundaries, drawn from diverse populations. Such a database may be used, for example, by normalizing a set of data relevant to the patient of interest onto a phantom tissue model. In this way, image data taken from a population may be used to derive the relevant bone quality and to optimize the engagement between the implant and the patient's bone.

Once the image data of at least one joint is obtained, bone quality information can be derived by a variety of methods for calculating or estimating bone properties from the imaging modalities previously described, including CT, X-ray, MRI, DEXA, etc.

By way of example, bone density and elastic modulus can be derived from a CT image (or data relating to the image) by correlating CT brightness to bone density and then to elastic modulus using Hounsfield values (also known as CT numbers). Bone density of both the proximal end of the tibia and the distal end of the femur can be calculated from CT brightness values using the following equations:

A) Proximal Tibia:
Hounsfield unit to density conversion:
$p=1.14e^{-4}+(9.16e^{-7})*(CT\ \#)$, where p is in g/mm$^3$
B) Distal Femur:
Hounsfield unit to density conversion:
$p=1.39e^{-4}+(1.205e^{-6})*(CT\ \#)$, where p is in g/mm$^3$ The elastic modulus of both the proximal end of the Libia and the distal end of the femur can be calculated from the derived density values by the following equations:

A) Proximal Tibia:
Density to modulus conversion:
$E=(1.2965e^8)*(\rho^{1.5})$, $0<p<0.001$ g/mm$^3$
$E=(3.790e^{12})*(p^3)$, $0.001<p<0.00173$ g/mm$^3$
B) Distal Femur:
Density to modulus conversion:
$E=(1.283e^9)*(p^{1.85})$, $0<p<0.001$ g/mm$^3$
$E=(3.790e^{12})*(p^3)$, $0.001<p<0.00173$ g/mm$^3$ The aforementioned models are only exemplary manners of deriving bone property information from the image data of at least one joint. Alternative and additional methods such as those disclosed in U.S. Pat. Pub. No. 2015/0080717, assigned to Applicant and incorporated in its entirety herein, or any other methods known in the art may be employed.

Figure 4:
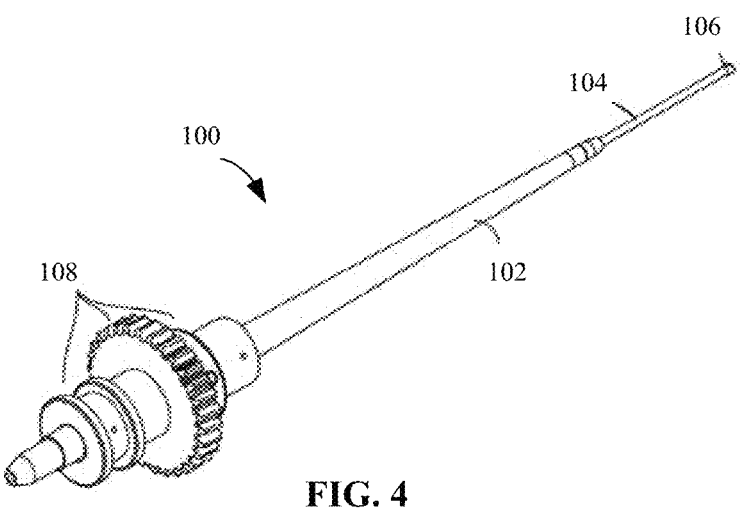
FIG. 4 is a perspective view of a fluid jet device according to an embodiment of the present invention.

After bone quality data has been determined, fluid jet 100, as shown in FIG. 4, may be operated by a surgeon to cut the bone, for example, to resect planned parameters 16, 16', 16". Fluid jet 100 may also be used to remove an implant having a quantified and known density using a traditional saw type cutting technique to make room for a revision implant.

Fluid jet 100 is particularly advantageous in cutting bone in preparation of a cementless implant fixation procedure as the cutting fluid, which may be water for example, keeps the cutting region cool and prevents bone necrosis. Moreover, in previous studies, water jet cutting has been shown to be more accurate and reproducible than traditional saw cutting during which the blades are susceptible to deflection. It is also contemplated that the cutting fluid could contain a saline solution for fighting bacteria and preventing infection.

Figure 5:
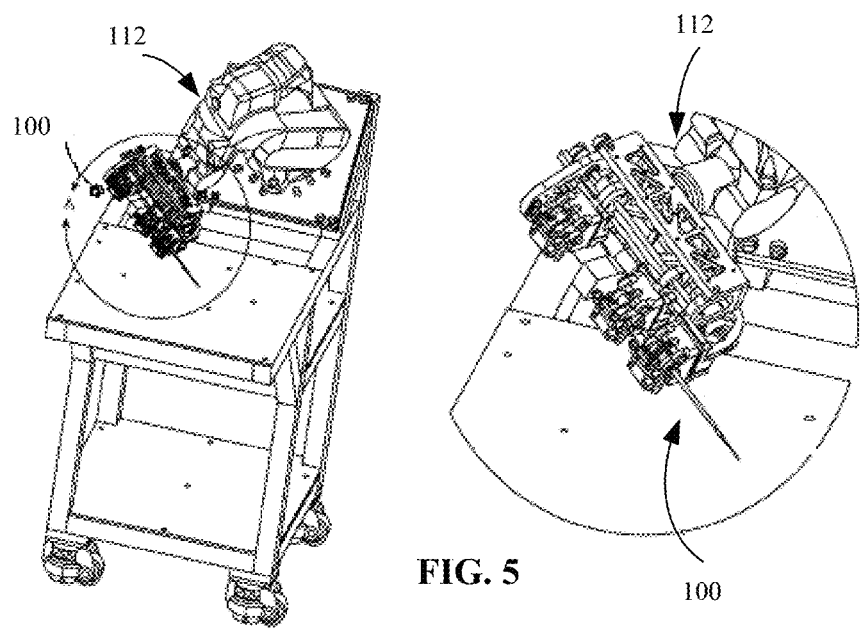
FIG. 5 is a perspective view of a robotic arm coupled to the water jet device of FIG. 4.

Fluid jet 100 generally includes a body 102, a hose 104 at least partially disposed within body 102, a nozzle 106 provided at a distal end of the hose, and an instrument drive coupling mechanism 108 provided at a proximal end of the body. The drive coupling mechanism is configured to couple fluid jet 100 to a robotic arm 112 as depicted in FIG. 5. For example, fluid jet 100 may be coupled to the RIO® robotic system, provided by MAKO Surgical Corp., the da Vinci® Surgical System, provided by Intuitive Surgical, Inc., the Magellan™ Robotic System, provided by Hansen Medical, Inc., Carnegie Mellon's Micron, or John Hopkins University's Steady Hand. In this preferred embodiment, placement of nozzle 106 is optimized by the robotic arm. However, fluid jet 100 may be manually operated in some instances, and therefore, need not include coupling mechanism 108. If manually operated, fluid jet 100 may instead include a navigation tool for spatial recognition.

Figure 6A:
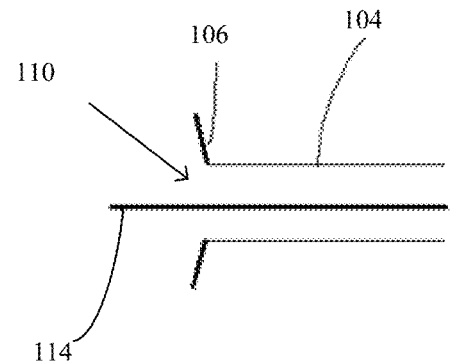
FIG. 6A is a cross-section view of a nozzle of the fluid jet device of FIG. 4 with the nozzle in a first position and the deflector in a first position.
Figure 6B:
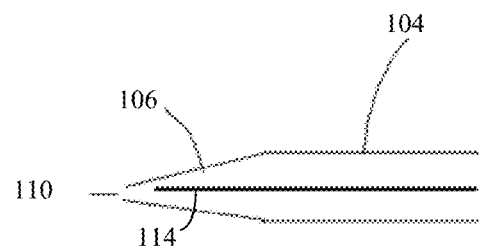
FIG. 6B is a cross-section view of a nozzle of the fluid jet device of FIG. 4 with the nozzle in a second position and the deflector in the first position.

Referring to FIGS. 6A and 6B, nozzle 106 is illustrated in more detail. A proximal end of nozzle 106 is pivotally connected to hose 104 such that a diameter of the nozzle opening 110 is adjustable. Specifically, nozzle 106 is moveable between a first position as shown in FIG. 6A to a second position as shown in FIG. 6B. The second position being relatively closed compared to the first position. By adjusting the diameter of the nozzle opening 110, a surgeon will have greater control over parameters such as a fluid cutting area, fluid cutting shape, fluid pressure levels, cut depth, and nozzle orientation. Nozzle 106 may be made from stainless steel or any other suitable medical grade metal or plastic known in the art.

Figure 6C:
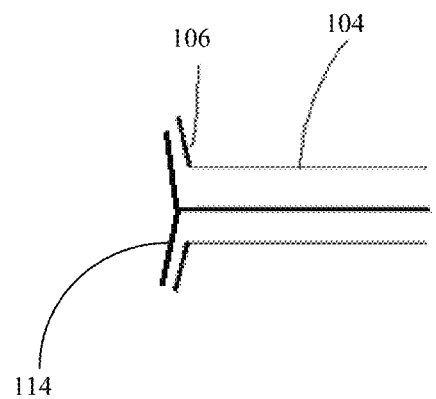
FIG. 6C is a cross-section view of the nozzle of the fluid jet device of FIG. 4 with the nozzle in the first position and the deflector in the second position.

Nozzle 106 may optionally include an adjustable deflector 114 for directing fluid flow radially outward. Deflector 114 is moveable between a first position (FIGS. 6A and 6B), in the deflector is arranged along, or parallel to, a longitudinal axis of nozzle 106, and a second position (FIG. 6C), in which the deflector has pivoted to a position transverse to the longitudinal axis of the nozzle. Deflector 114 may be adjusted from a position parallel to the longitudinal axis of nozzle 106 to a position perpendicular thereto, or any position in between. When deflector 114 is in the first position (e.g., parallel to the longitudinal axis of the nozzle), fluid flow is directed exclusively by nozzle 106. However, when deflector 114 transitions to the second position, transverse to the longitudinal axis of the nozzle, fluid flow is directed radially outward as a result of the deflector and nozzle 106 acting in concert. Nozzle 106 is thus advantageously capable of performing a variety of cuts, for example, straight or flat cuts and compacting/resecting an interior canal of the bone in the shape of the keel and pegs to support an implant, without compacting the bone along an axis of the long bone.

Figure 7A:
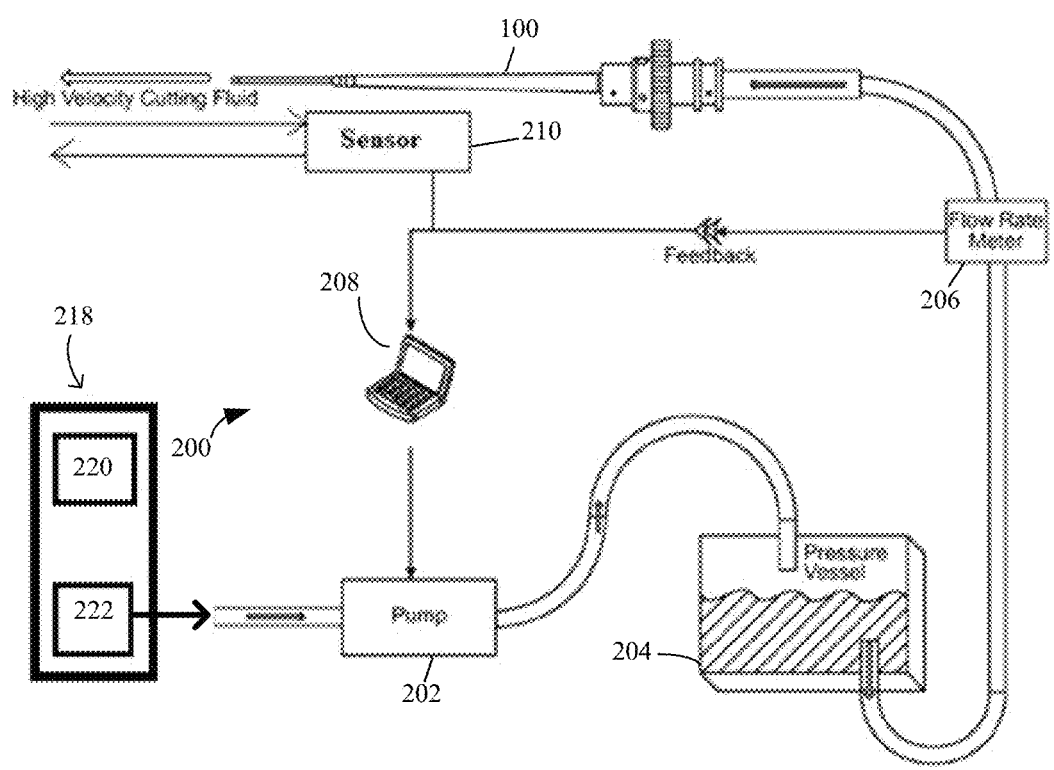
FIGS. 7A-7C are block diagrams of a water jet system, according to multiple embodiments of the present invention.
Figure 7B:
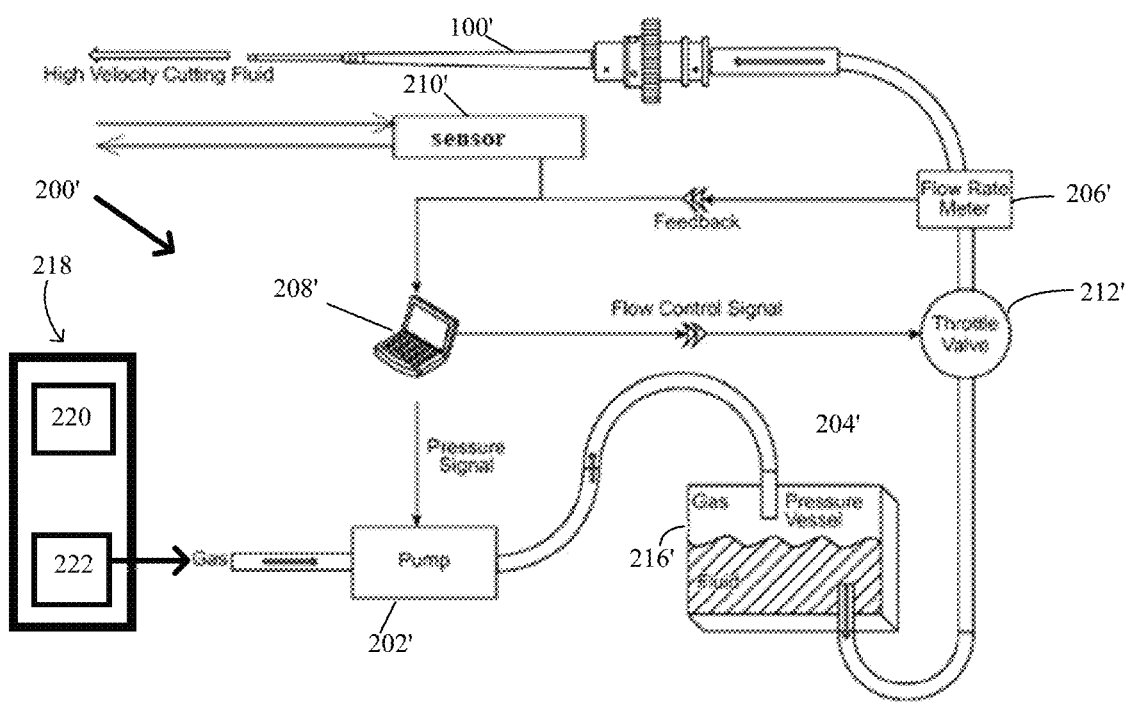
Figure 7C:
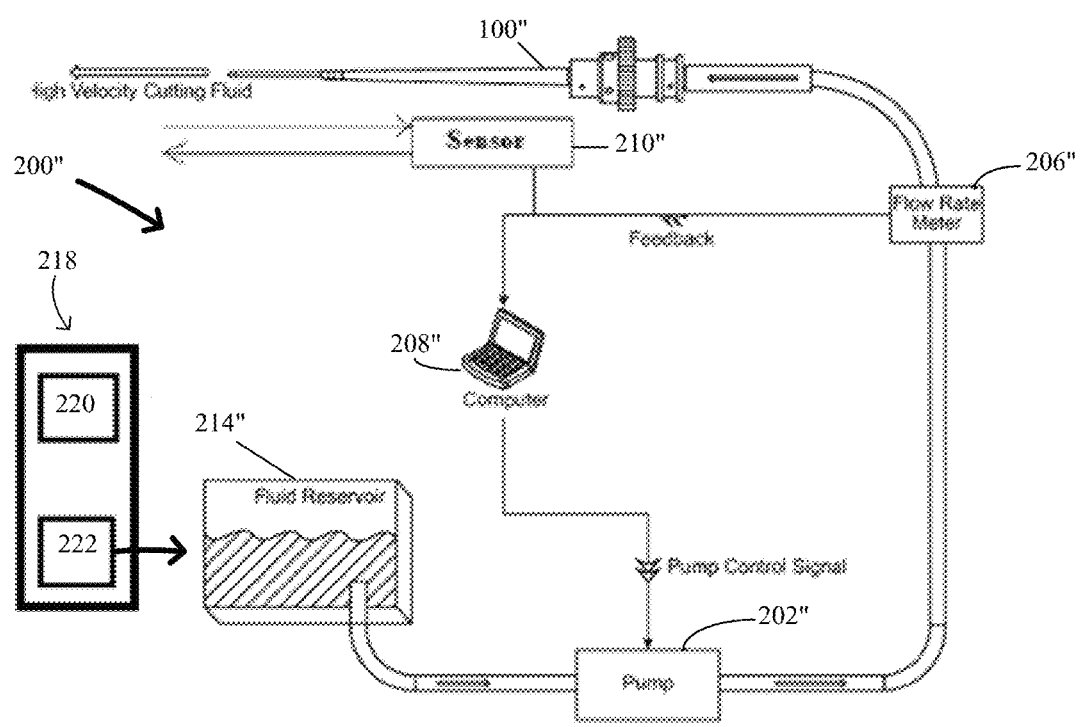

FIGS. 7A-7C illustrate exemplary block diagrams of a fluid jet system 200, 200', 200". Fluid jet device 100 may be incorporated into any of the fluid jet systems 200, 200', 200" shown in FIGS. 7A-7C.

In a preferred embodiment, in which fluid jet device 100 is controlled by robotic arm 112, further components of fluid jet systems 200, 200', 200", as explained hereinafter, are also coupled to robotic arm 112. In the manually controlled embodiment, fluid jet device 100 may be coupled to other components of fluid jet systems 200, 200'. 200" via an interface.

With specific reference to FIG. 7A, depicting fluid jet system 200, fluid enters a pump 202 and is forwarded to a pressure vessel 204 via a tube. An output of the pressure vessel is forwarded to the flow rate meter 206. An output of flow rate meter 206 and adjustment of the diameter of nozzle 106 is controlled by a feedback loop including controller 208 and pump 202. Controller 208 may be a computer, a central processing unit, a microcontroller, ASIC, or other control circuitry. Based upon the preoperatively obtained bone quality information, fluid flow is controlled throughout the cut of a particular section of bone. More particularly, cutting area, shape of the jet, and pressure, for example, of the cutting fluid can be precisely controlled via the continuous feedback loop and the preoperatively obtained bone quality data.

Since the bone quality data is preoperatively determined, the fluid jet pressure for cutting a particular section of bone can also be preoperatively determined. Advantageously, cutting pressure can be controlled via the feedback loop and the adjustable nozzle 106 such that flow rate meter 206 outputs a minimum pressure sufficient to cut a particular section of bone in order to minimize damage to the surrounding soft tissue. As bone is heterogeneous, the flow rate can be continuously adjusted to maintain minimum sufficient pressure throughout the depth of the cut as different density of bone is encountered.

Although fluid flow, including fluid pressure and the length of time the pressure must be applied to a particular cutting region to make a cut, can be preoperatively determined from the bone quality data, system 200 may optionally further include a sensor 210 for determining a cut depth. The sensor may be, for example, an ultrasonic sensor or an optical sensor for verifying the cut depth. A signal may be sent from the sensor 210 and reflected off of the cutting region of the bone such that real-time cutting depth information can be transmitted to controller 208 to verify accuracy and/or adjust the fluid flow, if necessary. Since the robot or a navigation system can track the locations at which the nozzle previously 'fired', the closed loop system is also capable of showing the user the resected bone and remaining bone sections, similar to the manual burr and saw tools used in the MAKO system.

Modified system 200', shown in FIG. 7B, is substantially similar to system 100' shown in FIG. 7A, in that the modified system includes a pump 202', a pressure vessel 204', a flow rate meter 206', a controller 208' and optionally, a sensor 210'. However, modified system 200' additionally includes of a throttle valve 212' that aids in regulating flow rate. In modified system 200', throttle valve 212' receives the control signal from controller 208'. Furthermore, modified system 200' may utilize a gas for controlling fluid flow, and thus, may include a pressure gauge 216' coupled to pressure vessel 204'.

Restructured system 200", shown in FIG. 7C, is substantially similar to system 200 shown in FIG. 7A, in that the restructured system includes a pump 202", a flow rate meter 206", a controller 208" and optionally, a sensor 210". However, restructured system 200" removes pressure vessel 204, 204' such that the feedback loop is only involves pump 202", flow rate meter 206" and controller 208".

Any of the fluid jet systems 200, 200', 200" may further include a reclaim system 218, including a vacuum 220 and a filter 222. Reclaim system 218 may be either integrated into fluid jet systems 200, 200', 200" or coupled thereto. Vacuum 220 being capable of suctioning excess water, bone chips/debris, blood and other waste products (collectively debris) from the surgical site during a resection. After removal from the surgical site, the water and debris is then forwarded to filter 222 where the water is separated from the debris. The debris is discarded and the water recycled to the fluid reservoir for re-use in the same surgery.

In use, system 200, 200', 200" is capable of cutting various types of bone and is particularly advantageous in preparing bone, for example, for knee, hip, and shoulder implants. After bone quality data, such as bone density, is preoperatively obtained, a specific fluid flow (e.g., cutting area, cutting shape, and fluid pressure) can be calculated for performing each of the desired resections.

Referring to FIG. 5, fluid jet 100 is then coupled to robotic arm 112 via instrument drive mechanism 108. Here, fluid jet 100 is precisely positioned via arm 112 coupled to a robotic system, for example, the RIO® robotic system, provided by MAKO Surgical Corp.

To perform a knee replacement, a series of flat cuts are made to remove the target bone from the femur using system 200, 200', 200". After the planar cuts have been made, nozzle 106 may be adjusted and the bone of the tibia can be radially compacted in the shape of the keel and pegs to prepare the metaphyseal bone to receive the implant.

To perform a hip replacement, system 200, 200', 200" may be used to etch through cartilage and bone and subsequently to cut though the femoral neck. Depending on the type of implant being used, cemented or cementless, bone will either need to be compacted or removed to allow for cement integration. By controlling fluid jet 100, and particularly, the fluid cutting area, shape, and any of the numerous desired resections can be performed. Based in part on the preoperatively obtained bone quality data, and the previously described feedback loops, system 200, 200'. 200" is capable of continuously controlling the fluid flow throughout the depth of a cut. Increasing and decreasing fluid pressure, for example, throughout the cut allows system 200, 200', 200" to utilize a minimum pressure sufficient to cut through different densities of the heterogeneous bone so as to minimize damage to the ligaments and soft tissue surrounding the cutting site.

During the resection, vacuum 220 may be placed proximate the surgical site for removing water and debris therefrom. Although reclaim system 218 is advantageous in any surgery, reclaim system 218 is particularly critical in total hip replacements for ensuring that bone chips are removed from the surgical site and not deflected into areas between soft tissue which could result in heterotopic ossification.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, features or steps described in relation to one aspect of the disclosure may be combined with features or steps described in relation to another aspect of the disclosure. In addition, although methods may be described as having a number of steps, the steps do not need to be completed in the exact order described, unless explicitly noted otherwise or required by the context of the steps.

The invention claimed is:

1. A surgical cutting system, comprising:
   a bone resection tool including a nozzle having an adjustable diameter; and
   a controller operable to adjust the diameter of the nozzle to vary fluid flow and control an amount of bone removed from a workpiece by the bone resection tool, wherein the controller is adapted to adjust the nozzle diameter to control fluid pressure throughout a depth of a resection as different density of bone is encountered based on a position of the nozzle relative to the workpiece and bone quality data preoperatively obtained from the workpiece, and wherein the controller is adapted to provide minimal fluid pressure sufficient to cut through respective bone densities as each of the different bone densities is encountered.

2. The system of claim 1, wherein the bone resection tool is coupled to a robotic arm via a drive mechanism.

3. The system of claim 1, further comprising a feedback loop including a sensor continuously providing cut depth information, and wherein the controller is further adapted to adjust the nozzle to vary the fluid flow based upon the cut depth information.

4. The system of claim 3, wherein the feedback loop further comprises at least one of a flow rate meter, a pump, a pressure gauge, and a throttle valve for facilitating control of the fluid flow.

5. The system of claim 1, wherein the bone quality data includes at least one of bone density, porosity, and elastic modulus.

6. The system of claim 5, wherein the bone quality data is derived from image data.

7. The system of claim 6, wherein the image data is CT image data.

8. The system of claim 5, wherein the bone quality data is derived from a single individual.

9. The system of claim 1, further comprising a fluid reservoir coupled to the bone resections tool.

10. The system of claim 9, further comprising a saline solution disposed in the fluid reservoir.

11. The system of claim 1, wherein the nozzle further comprises a deflector for directing fluid flow radially outward.

12. A method of cutting bone comprising:
   obtaining bone quality data;
   operating a bone removal tool including a nozzle having an adjustable diameter, the bone removal tool coupled to a robotic arm via an instrument drive mechanism; and
   controlling the diameter of the nozzle to control fluid pressure throughout a depth of a resection as different density of bone is encountered based on a position of the nozzle and the obtained bone quality data, and wherein the controlling step further comprises providing minimal fluid pressure sufficient to cut through respective bone densities as each of the different bone densities is encountered.

13. The method of claim 12, further comprising continuously sensing cut depth information via a sensor and wherein the controlling step is further based on the cut depth information.

14. The method of claim 13, wherein the sensor is an ultrasonic sensor or an optical sensor.

15. The method of claim 12, further comprising deflecting the fluid flow in a radially outward direction.

16. The method of claim 12, wherein the bone quality data is obtained preoperatively.

17. The method of claim 12, wherein the bone quality data comprises at least one of bone density, porosity, and elastic modulus.

18. The method of claim 12, wherein the step of operating the bone removal tool comprises spatially moving the nozzle relative to the bone.

19. The method of claim 12, wherein the step of obtaining bone quality data includes calculating one or more Houndsfield values from CT image data.

* * * * *